United States Patent
Kan et al.

(10) Patent No.: US 9,700,511 B2
(45) Date of Patent: Jul. 11, 2017

(54) CONTROLLED DRUG RELEASE LIPOSOME COMPOSITION

(71) Applicants: TAIWAN LIPOSOME COMPANY, LTD, Taipei (TW); TLC BIOPHARMACEUTICALS, INC., South San Francisco, CA (US)

(72) Inventors: Pei Kan, Taipei (TW); Yun-Long Tseng, Taipei (TW); Han Chun Ou, Taipei (TW)

(73) Assignees: TLC Biopharmaceuticals, Inc., South San Francisco, CA (US); Taiwan Liposome Company, Ltd., Taipei (TW)

( * ) Notice: Subject to any disclaimer, the term of this patent is extended or adjusted under 35 U.S.C. 154(b) by 0 days.

(21) Appl. No.: 14/774,833

(22) PCT Filed: Mar. 15, 2014

(86) PCT No.: PCT/US2014/029907
§ 371 (c)(1),
(2) Date: Sep. 11, 2015

(87) PCT Pub. No.: WO2014/145187
PCT Pub. Date: Sep. 18, 2014

(65) Prior Publication Data
US 2016/0030340 A1 Feb. 4, 2016

Related U.S. Application Data

(60) Provisional application No. 61/792,850, filed on Mar. 15, 2013.

(51) Int. Cl.
*A61K 9/127* (2006.01)
*A61K 31/337* (2006.01)
(Continued)

(52) U.S. Cl.
CPC ............ *A61K 9/127* (2013.01); *A61K 31/337* (2013.01); *A61K 31/475* (2013.01);
(Continued)

(58) Field of Classification Search
None
See application file for complete search history.

(56) References Cited

U.S. PATENT DOCUMENTS

2001/0051183 A1   12/2001   Martin
2007/0116753 A1*   5/2007   Hong ................... A61K 9/0019
                                                  424/450

(Continued)

FOREIGN PATENT DOCUMENTS

CN   1771954 A    5/2006
CN   1839800 A   10/2006

(Continued)

OTHER PUBLICATIONS

G Zhu, E Oto, J Vaage, Y Quinn, M Newman, C Engbers, P Uster. "The effect of vincristine—polyanion complexes in STEALTH liposomes on pharmacokinetics, toxicity and anti tumor activity." Cancer Chemotherapy and Pharmacology, vol. 39, 1996, pp. 138-142.*
CAS Registry Record for Irinotecan (Cas# 97682-44-5). Entered STN Aug. 18, 1985, downloaded by examiner on Apr. 14, 2016, 2 printed pages.*
International Search Report issued in corresponding International Application No. PCT/US2014/029907 on Aug. 8, 2014.

(Continued)

*Primary Examiner* — Isaac Shomer
(74) *Attorney, Agent, or Firm* — Seed IP Law Group LLP

(57) ABSTRACT

The present invention relates to a pharmaceutical composition comprising at least one liposome, at least one polyvalent counterion donor or a pharmaceutically acceptable salt thereof, at least one monovalent counterion donor or a pharmaceutically acceptable salt thereof, and an amphipathic therapeutic agent. The present invention also relates to methods of inhibiting cancer cell growth, comprising administering the pharmaceutical composition described herein.

3 Claims, 2 Drawing Sheets

(51) Int. Cl.
- A61K 31/4745 (2006.01)
- A61K 31/475 (2006.01)
- A61K 31/704 (2006.01)
- A61K 31/7048 (2006.01)

(52) U.S. Cl.
CPC ........ *A61K 31/4745* (2013.01); *A61K 31/704* (2013.01); *A61K 31/7048* (2013.01); *Y10S 977/907* (2013.01)

(56) References Cited

U.S. PATENT DOCUMENTS

| | | | |
|---|---|---|---|
| 2009/0081121 A1* | 3/2009 | Ting | A61K 51/1234 424/1.21 |
| 2012/0171283 A1 | 7/2012 | Hong | |

FOREIGN PATENT DOCUMENTS

| | | |
|---|---|---|
| CN | 101849915 A | 10/2006 |
| CN | 1980637 A | 6/2007 |
| CN | 100998562 A | 7/2007 |
| CN | 101129375 A | 2/2008 |
| CN | 101843584 A | 9/2010 |
| CN | 101933904 A | 1/2011 |
| WO | 03/018018 A2 | 3/2003 |
| WO | 2004/105782 A2 | 12/2004 |
| WO | 2005107712 A1 | 11/2005 |
| WO | 2007/049278 A2 | 5/2007 |
| WO | 2011/092708 A2 | 8/2011 |

OTHER PUBLICATIONS

Drummond, et al. Improved Pharmacokinetics and Efficacy of a Highly Stable Nanoliposomal Vinorelbine, JPET 328:321-330, 2009.

Zhang, et al. A lipid microsphere vehicle for vinorelbine: Stability, safety and pharmacokinetics, International Journal of Pharmaceutics 348 (2008) 70-79.

Harasym, et al. Sphingomyelin-cholesterol liposomes significantly enhance the pharmacokinetic and therapeutic properties of vincristine in murine and human tumour models, British Journal of Cancer (1995) 72, 896-904.

Rao et al. Pharmacokinetics, efficacy and toxicity of different pegylated liposomal doxorubicin formulations in preclinical models: is a conventional bioequivalence approach sufficient to ensure therapeutic equivalence of pegylated liposomal doxorubicin products? Cancer Chemother Pharmacol (2010) 66:1173-1184.

Johnston, et al. Therapeutically optimized rates of drug release can be achieved by varying the drug-to-lipid ratio in liposomal vincristine formulations; Biochimica et Biophysica Acta 1758 (2006) 55-64.

Semple et al. Optimization and Characterization of a Sphingomyelin/ Cholesterol Liposome Formulation of Vinorelbine with Promising Antitumor Activity; Journal of Pharmaceutical Sciences, vol. 94, No. 5, May 2005.

Zhigaltsev, et al. Liposome-encapsulated vincristine, vinblastine and vinorelbine: A comparative study of drug loading and retention; Journal of Controlled Release 104 (2005) 103-111.

Zhigaltsev et al. Formation of drug—arylsulfonate complexes inside liposomes: A novel approach to improve drug retention; Journal of Controlled Release 110 (2006) 378-386.

* cited by examiner

CONTROLLED DRUG RELEASE LIPOSOME COMPOSITION

CROSS REFERENCE TO RELATED APPLICATIONS

This application is a national stage under 35 U.S.C. 371 based on and claiming the benefit of International Application PCT/US2014/029907 filed on Mar. 15, 2014, which claims the benefit of priority from U.S. Provisional Application No. 61/792,850, filed Mar. 15, 2013, the entire contents of each of which are incorporated herein by reference.

TECHNOLOGY FIELD

The present invention relates to a pharmaceutical composition comprising at least one liposome, at least one polyvalent counterion donor or a pharmaceutically acceptable salt thereof, at least one monovalent counterion donor or a pharmaceutically acceptable salt thereof, and a therapeutic agent.

BACKGROUND OF THE INVENTION

Liposomes have been widely used as an in vivo carrier of various therapeutic agents. Ideally, such liposomes should have a high encapsulating efficiency and an extended retention profile (i.e. minimal release of the drug before reaching the targeted site).

NanoVNB® product is a liposomal vinorelbine, which utilizes liposome to enhance the retention of vinorelbine before it reaches the targeted site. Phase I clinical trial of NanoVNB® product did show enhanced anti-cancer efficacy, but the extended retention of vinorelbine in vivo also lead to increased toxicity.

Therefore, there is a need to provide a liposomal composition that is useful for delivery of a therapeutic agent with an adjustable retention profile, to obtain a balance between optimal anti-cancer efficacy and minimal side effect. The present invention addresses this need, as well as other important needs.

BRIEF SUMMARY OF THE INVENTION

In one embodiment, the present invention is directed to a pharmaceutical composition comprising at least one liposome, at least one polyvalent counterion donor or a pharmaceutically acceptable salt thereof, at least one monovalent counterion donor or a pharmaceutically acceptable salt thereof, and a therapeutic agent, a derivative thereof, or a pharmaceutically acceptable salt thereof. Advantageously, this pharmaceutical composition provides an adjustable retention profile and an adjustable encapsulation percentage of the therapeutic agent.

In another embodiment, the present invention provides a pharmaceutical composition, comprising at least one liposome having a particle forming component selected from a phospholipid or a mixture of at least one phospholipid and cholesterol; 0.1 mM to 10 mM polyvalent counterion donor or a pharmaceutically acceptable salt thereof; 150 mM to 450 mM monovalent counterion donor or a pharmaceutically acceptable salt thereof; and a vinca alkaloid.

In a third embodiment, the present invention provides a pharmaceutical composition, comprising at least one liposome having a particle forming component selected from a phospholipid or a mixture of at least one phospholipid and cholesterol; 1 milliequivalent (mEq) to 320 mEq polyvalent counterion donor or a pharmaceutically acceptable salt thereof; 150 mM to 450 mM monovalent counterion donor or a pharmaceutically acceptable salt thereof; and an amphipathic therapeutic agent.

The present invention is also directed to methods of inhibiting cancer cell growth in a subject in need thereof. The method comprises administering a pharmaceutical composition described herein, wherein the symptoms and signs of cancer in the subject are reduced. Advantageously, this method enhances cancer cell inhibition and reduces toxicity.

Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

The invention will become more apparent when read with the accompanying figures and detailed description which follow.

DETAILED DESCRIPTION OF THE INVENTION

Definitions

Figure 1:
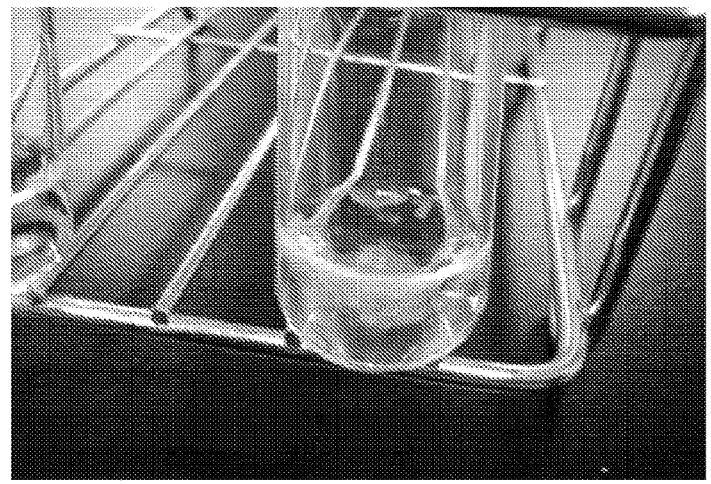
FIG. 1 shows precipitation of sodium dextran sulfate and vinorelbine in the liposome.

As employed above and throughout the disclosure, the following terms, unless otherwise indicated, shall be understood to have the following meanings.

As used herein, the singular forms "a," "an," and "the" include the plural reference unless the context clearly indicates otherwise.

An "effective amount," as used herein, includes a dose of the pharmaceutical composition that is sufficient to reduce the symptoms and signs of cancer, which include, but are not limited to, weight loss, pain and tumor mass, which is detectable, either clinically as a palpable mass or radiologically through various imaging means.

The term "treating," "treated," or "treatment" as used herein includes preventative (e.g. prophylactic), palliative, and curative uses or results.

The term "inhibiting" and "suppressing" includes slowing or stopping the growth of.

The term "subject" can refer to a vertebrate having cancer or to a vertebrate deemed to be in need of cancer treatment. Subjects include warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

The term "counterion donor" includes a counterion donor capable of forming a salt with a therapeutic agent and does not reduce the activity of the therapeutic agent. In one embodiment, the therapeutic agent is an amphipathic acid with a net negative charge, the counterion donor is a cationic ion or an entity covalently linked to one or more cationic functional groups. In another embodiment, the therapeutic agent is an amphipathic base with a net positive charge, the counterion donor is an anionic ions or an entity covalently linked to one or more anionic functional groups. The counterion donor has high solubility in the agent carrying component of the liposome, but a low liposome membrane (bilayer) permeability. Therefore, the counterion donor is retained in the agent-carrying component during loading of the therapeutic agent, and during storage.

All numbers herein may be understood as modified by "about."

As used herein, the term "alkyl" refers to a straight or branched, saturated, aliphatic radical having from 1 to about 10 carbon atoms. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, and decyl.

As used herein, the term "aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be 15 monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 to 20 ring members, such as phenyl. "Substituted aryl" groups can be substituted with one or more groups selected from halo, hydroxy, amino, alkylamino, amido, acyl, nitro, cyano, and alkoxy.

"Pharmaceutically acceptable salts" of an amphipathic acid of the present invention are salts formed with bases, namely cationic salts such as alkali and alkaline earth metal salts, such as sodium, lithium, potassium, calcium, magnesium, as well as 4 ammonium salts, such as ammonium, trimethyl-ammonium, diethylammonium, and tris-(hydroxymethyl)-methyl-ammonium salts.

Similar acid addition salts, such as of mineral acids, organic carboxylic and organic sulfonic acids, e.g., hydrochloric acid, methanesulfonic acid, maleic acid, are also possible provided to a basic therapeutic agent with a constitute such as pyridyl, as part of the structure.

Liposome

The term "liposome" as used herein means multivesicular liposome (MVL), multilamellar vesicles (MLU) or small or large unilamellar vesicles (ULV). The liposomes are nano-sized and comprise a particle-forming component and an agent-carrying component. The particle-forming component forms an enclosed lipid barrier, and the agent carrying component comprises a medium enclosed by the particle-forming component.

The particle forming component can be prepared from a phospholipid or a mixture of at least one phospholipid, and cholesterol. Examples of the phospholipid used in the present invention include, but are not limited to, phosphatidylcholine (PC), phosphatidylglycerol (PG), phosphatidylethanolamine (PE), phosphatidylserine (PS), phosphatidic acid (PA), phosphatidylinositol (PI), egg phosphatidylcholine (EPC), egg phosphatidylglycerol (EPG), egg phosphatidylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI), dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), dioleoylphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleoylphosphatidylethanolamine (DOPE), palmitoylstearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC), distearoylphosphatidylethanolamine (DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoylphosphatidylinositol (DPPI), 1,2-dioleoyl-sn-glycero-3-phosphatidylinositol (DOPI), dimyristoylphosphatidylinositol (DMPI), distearoylphosphatidylinositol (DSPI), and a mixture thereof.

In one embodiment, the particle-forming component is free of fatty acid or cationic lipid (i.e. a lipid carrying a net positive charge at physiological pH).

In another embodiment, the particle-forming component includes a hydrophilic polymer with a long chain of highly hydrated flexible neutral polymer attached to a phospholipid molecule. Without being bound by any theory, the hydrophilic polymer is believed to stabilize the liposome and result in a longer circulation time in vivo. Examples of the hydrophilic polymer include, but are not limited to, polyethylene glycol (PEG) with a molecular weight about 2,000 to about 5,000 daltons, methoxy PEG (mPEG), ganglioside $GM_1$, polysialic acid, polylactic (also termed polylactide), polyglycolic acid (also termed polyglycolide), apolylacticpolyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose and synthetic polymers.

In one group of embodiment, the phospholipids are selected from DSPC and DSPE-PEG, wherein the molecular weight of PEG is about 2,000 daltons (hereafter DSPE-$PEG_{2000}$).

In another group of embodiment, the molar ratio of DSPC, cholesterol and DSPE-$PEG_{2000}$ is about 3:2:0.45.

The particle-forming component may further comprise a lipid-conjugate of an antibody or a peptide that acts as a targeting moiety to enable the liposome to specifically bind to a target cell bearing a target molecule. Examples of the target molecules include, but are not limited to, epidermal growth factor receptor (EGFR), vascular endothelial growth factor receptor (VEGFR), carcinoembryonic antigen (CEA), and erbB-2/neu (HER2).

The liposomes have a mean particle diameter of about 30 nm to about 200 nm, more preferably about 50 nm to about 150 nm.

The liposomes prepared in this invention can be generated by conventional techniques used to prepare vesicles. These techniques include the ether injection method (Deamer et al., *Acad. Sci.* (1978) 308: 250), the surfactant method (Brunner et al., *Biochim. Biophys. Acta* (1976) 455: 322), the freezethaw method (Pick et al., *Arch. Biochim. Biophys.* (1981) 212: 186), the reverse-phase evaporation method (Szoka et al., *Biochim. Biophys. Acta.* (1980) 601: 559 71), the ultrasonic treatment method (Huang et al., *Biochemistry* (1969) 8: 344), the ethanol injection method (Kremer et al., *Biochemistry* (1977) 16: 3932), the extrusion method (Hope et al., *Biochim. Biophys. Acta* (1985) 812:55 65), the French press method (Barenholz et al., *FEBS Lett.* (1979) 99: 210) and methods detailed in Szoka, F., Jr., et al., *Ann. Rev. Biophys. Bioeng.* 9:467 (1980). All of the above processes are basic technologies for the formation of liposome vesicles and these processes are incorporated by reference herein.

Therapeutic Agent

The therapeutic agent may be of any appropriate therapeutic agent. In one embodiment, the therapeutic agent is an anti-cancer agent. Non limiting examples of anti-cancer agent include vinca alkaloid, topoisomerase inhibitor, taxane compound, a derivative thereof, or a pharmaceutically acceptable salt thereof.

Examples of vinca alkaloid include, but are not limited to, vinorelbine, vincristine, vinblastine and vindestine.

Examples of topoisomerase inhibitor include, but are not limited to, topotecan, camptothecin, irinotecan, etoposide and doxorubicin.

Examples of taxane compound include, but are not limited to, paclitaxel.

The Monovalent Counterion Donor

In one embodiment, the therapeutic agents are amphipathic bases with a net positive charge, the monovalent counterion donor within the liposome may be selected from an anionic ion or an entity which is covalently linked to an anionic functional group. The anionic ion or the anionic functional group has a valency of −1, −2, or −3.

Non limiting examples of monovalent counterion donor include benzenesulfonic acid and 4-hydroxybenzenesulfonic acid, as illustrated below:

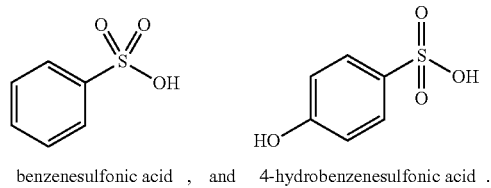 [SMILES: O=S(=O)(O)c1ccccc1 ; O=S(=O)(O)c1ccc(O)cc1]

benzenesulfonic acid , and   4-hydrobenzenesulfonic acid .

In another embodiment, the pharmaceutically acceptable salt of the monovalent counterion donor comprises a) an anionic ion or an entity which is covalently linked to an anionic functional group; and b) one or more cationic ions, wherein the anionic ion or the anionic functional group is ionically paired with the cationic ions.

The anionic ion or the anionic functional group can be selected from one or more of the following: citrate, sulfate, sulfonate, phosphate, pyrophosphate, tartrate, succinate, maleate, borate, carboxylate, glucoronate, chloride, hydroxide, nitrate, cyanate or bromide. In one embodiment, the anionic ion and the anionic functional group is selected from one or more of the following: citrate, sulfate, sulfonate, phosphate, pyrophosphate, or carboxylate.

In yet another embodiment, the entity linked to the anionic functional group can be a natural or synthetic, organic or inorganic compound. Examples of the entity include, but are not limited to, non-polymer such as benzene, oligonucleotide and monosaccharide, or polymer such as polyvinyl, polyol such as glycerol, sorbitol and mannitol, polysaccharide, polypeptides, glycoproteins and polynucleotide.

The cationic ion of the pharmaceutically acceptable salt can be selected from one or more of the following: calcium ion, magnesium ion, sodium ion, potassium ion, manganese ion, or $NR_4^+$, wherein R is H or an organic residue such as alkyl or aryl, or a mixture thereof. In one embodiment, the cationic ion is ammonium.

A second embodiment of the present invention provides for an amphipathic acidic therapeutic agent, and a monovalent counterion donor within the liposome may be selected from includes a cationic ion or an entity which is covalently linked to a cationic functional group. The cationic ion or the cationic functional group has a valency of +1, +2, or +3.

The pharmaceutically acceptable salt of the monovalent counterion donor comprises a) a cationic ion or an entity which is covalently linked to a cationic functional group; and b) one or more anionic ion, wherein the cationic ion or the cationic functional group is ionically paired with one or more anionic ions.

In one embodiment, the monovalent counterion donor is ammonium sulfate. In another embodiment, the concentration of the monovalent counterion donor is about 100 to about 500 mM, or any value or ranges therebetween in 10 mM increments (e.g. 80 mM, 320 mM). In yet another embodiment, the concentration of the monovalent counterion donor is about 150 to about 450 mM, In yet another embodiment, the concentration of the monovalent counterion donor is about 200 mM to about 400 mM. In yet another embodiment, the concentration of the monovalent counterion donor is about 300 mM.

The Polyvalent Counterion

In one embodiment, the therapeutic agent is an amphipathic base, and at least one polyvalent counterion donor or a pharmaceutically acceptable salt thereof forms an insoluble salt within the liposome.

In another embodiment, a polyvalent counterion donor includes an entity which is covalently linked with more than one anionic functional groups, wherein the anionic functional group has a valency of −1, −2, or −3. A pharmaceutically acceptable salt of a polyvalent counterion donor comprises a) an entity covalently linked to more than one anionic functional groups; and b) one or more cationic ions, wherein the anionic functional group is ionically paired with the cationic ions.

The anionic functional group of the polyvalent counterion is selected from one or more of the following: citrate, sulfate, sulfonate, phosphate, pyrophosphate, tartrate, succinate, maleate, borate, carboxylate, glucoronate, chloride, hydroxide, nitrate, cyanate, or bromide. In one embodiment, the anionic functional group is selected from one or more of the following: citrate, sulfate, sulfonate, phosphate, pyrophosphate, or carboxylate. Each of the anionic functional groups of a polyvalent counterion donor can be different from each other. For example, chondroitin sulfate is a polyvalent counterion donor with different anionic functional groups on the same entity, as illustrated below:

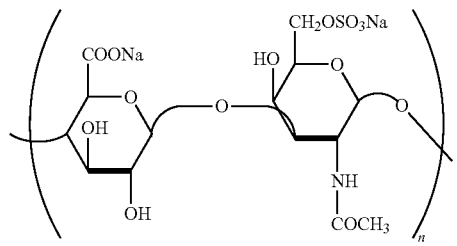

The cationic ion can be selected from one or more of the following: calcium ion, magnesium ion, sodium ion, potassium ion, manganese ion, $NR_4^+$, wherein R is H or an organic residue such as alkyl or aryl, and mixtures thereof. In one embodiment, the cationic ion is ammonium.

Another embodiment of the invention provides for an amphipathic acidic therapeutic agent, and a polyvalent counterion donor within the liposome includes an entity which is covalently linked to more than one cationic functional groups and said cationic group has a valency of +1, +2, or +3. The amphipathic acid forms an insoluble salt with the polyvalent counterion donor and is trapped inside the liposome.

The pharmaceutically acceptable salt of the polyvalent counterion donor comprises a) an entity which is covalently linked to one or more cationic functional groups; and b) one or more anionic ion, wherein the cationic functional group is ionically paired with the anionic ions.

The entity of the polyvalent counterion donor can be a natural or synthetic, organic or inorganic compound. Non-limiting examples of the entity include non-polymer such as oligonucleotide and monosaccharide, or polymer such as polyvinyl, polyols such as glycerol, sorbitol and mannitol, polysaccharides such as dextran and chitosan, polypeptides, glycoproteins and polynucleotides.

In one embodiment, the polyvalent counterion donor is selected from one or more of the following: sulfated heparin, carrageenan, mucin, sulfated hyaluronic acid, chondroitin sulfates, keratin sulfates, dermatan sulfates or sulfated polysaccharide. Non limiting example of sulfated polysaccharide includes dextran sulfate, with a molecular weight about 1,600 daltons to about 8,000 daltons.

In one embodiment, the pharmaceutically acceptable salt of dextran sulfate is selected from ammonium dextran sulfate or sodium dextran sulfate.

The Pharmaceutical Composition

In one embodiment, the pharmaceutical composition of the present invention comprises a combination of a) at least one liposome having a particle forming component selected from a phospholipid or a mixture of at least one phospholipid, and cholesterol, b) at least one polyvalent counterion donor or a pharmaceutically acceptable salt thereof; (c) at least one monovalent counterion donor or a pharmaceutically acceptable salt thereof; and (d) an amphipathic therapeutic agent, a derivative thereof, or a pharmaceutically acceptable salt thereof.

In another embodiment, the pharmaceutical composition of the present invention comprises a combination of a) at least one liposome having a particle forming component selected from a mixture of one or more phospholipids, and cholesterol, b) at least one polyvalent counterion donor or a pharmaceutically acceptable salt thereof with a concentration between about 0.1 mM to about less than 10 mM; (c) at least one monovalent counterion donor or a pharmaceutically acceptable salt thereof with a concentration of about 150 mM to about 450 mM; and (d) a vinca alkaloid. In yet another embodiment, the particle forming component further comprises a hydrophilic polymer.

Advantageously, by combining a polyvalent counterion donor or a pharmaceutically acceptable salt thereof, and a monovalent counterion donor or a pharmaceutically acceptable salt thereof, the encapsulation efficiency and/or retention profile of the therapeutic agent can be adjusted to maintain therapeutic efficiency, yet minimize toxicity.

In one group of embodiments, the anionic functional groups of the polyvalent counterion donor or its pharmaceutically acceptable salt have a total equivalent of valency about 1 to about 160 milliequivalent (mEq), about 3 to 160 mEq, about 1 to about 320 mEq, about 1 to about 250 mEq, about 3 to about 250 mEq, about 160 to about 250 mEq, or any value or ranges between 1 to 320 mEq in 1 mEq increments (e.g. 23 mEq, 233 mEq). In another embodiment, the anionic functional group of the polyvalent counterion donor or its pharmaceutically acceptable salt is sulfate.

In another group of embodiments, the concentration of the polyvalent counterion donor or its pharmaceutically acceptable salt is about 2 mM to less than 8 mM, about 0.1 mM to less than 8 mM, about 0.1 mM to less than about 10 mM, about 2 mM to less than 10 mM, or any value or ranges between 0.1 mM to 10 mM in 0.1 mM increments (e.g. 1.5 mM, 8.3 mM).

The pharmaceutical composition is formulated for any suitable administering routes including intracranial, intracerebral, intraventricular, intrathecal, intraspinal, oral, topical, rectal, transdermal, subcutaneous, intravenous, intramuscular intranasal, intraperitoneum, intratumor and the like.

The dosage of the pharmaceutical composition of the present invention can be determined by the skilled person in the art according to the embodiments. Unit doses or multiple dose forms are contemplated, each offering advantages in certain clinical settings. According to the present invention, the actual amount of the pharmaceutical composition to be administered can vary in accordance with the age, weight, general condition of the subject to be treated, the type of cancer, toxicity, and depends on the discretion of medical professionals.

In some embodiments, at least a portion of the therapeutic agent (such as vinorelbine) forms a salt with the pharmaceutically acceptable salt of polyvalent counterion donor and precipitates in the intraliposomal aqueous core, as evident in FIG. 1.

The Method of Inhibiting Cancer Cell Growth

The invention is directed to methods of inhibiting cancer cell growth in a subject, which comprises administering an effective amount of the pharmaceutical composition described herein to a subject in need thereof, whereby the symptoms and signs of the cancer and/or toxicity in the subject are reduced.

The pharmaceutical composition may be administered alone, or as an adjuvant to surgery, e.g., before surgery to reduce the tumor size and/or following surgery to reduce the possibility of metastases, e.g., by inhibit the growth and migration of circulating tumor cells through the blood stream.

The pharmaceutical composition can be administered before, after or simultaneously with one or more anti-cancer agents. The anti-cancer agent includes conventional chemotherapeutic agent, target cancer therapy or radiation therapy.

The conventional chemotherapeutic agent comprises DNA synthesis inhibitor, alkylating agent, antifolate agent, metabolic inhibitor or combination thereof.

The target cancer therapy are medications which inhibit the growth of cancer cells by interfering with specific targeted molecules needed for carcinogenesis and cancer growth, rather than by simply interfering with rapidly dividing cells (e.g. with conventional chemotherapeutic agent). The target cancer therapy comprises kinase inhibitor, angiogenesis inhibitor, epidermal growth factor receptor (EGFR) inhibitor, HER2/neu receptor or the combination thereof.

The radiation therapy uses high-energy radiation to shrink tumor and kill cancer cells. Examples of radiation therapy include X-ray, gamma rays, and charged particles.

The following examples further illustrate the present invention. These examples are intended merely to be illustrative of the present invention and are not to be construed as being limiting.

Example 1

Preparation of Liposomes

The liposomes were prepared by the solvent injection method. The lipids, including DSPC, DSPE-PEG$_{3000}$ and cholesterol, were combined at a molar ratio of 3:0.045:2 and dissolved in 99.9% ethanol at about 60° C. in a flask. A tabletop ultrasonic bath was used for lipid dissolution.

The dissolved lipid solution was added to the 1.0 mM sodium phosphate solution at 100 mL/min by a peristaltic pump and the two solutions were mixed. The lipid mixture was then passed 6-10 times through a polycarbonate membrane with a pore size of 0.2 um and 0.1 um, respectively. Liposomes (or large multilamellar vesicles) were formed and the average vesicle diameter was about 100-120 nm (measured by Malvern ZetaSizer Nano ZS-90).

The liposome mixture was dialyzed and concentrated by a tangential flow filtration system against by 0.9% (w/w) sodium chloride and 9% (w/w) sucrose solution with Millipore Pellicon 2 Mini Ultrafiltration Module Biomax-100C (0.1 m$^2$), and then sterilized using a 0.2 um sterile filter.

Example 2

Effect of Monovalent Counterion Donor on the Encapsulation Efficiency and Retention Profile The pharmaceutical composition was prepared by mixing the liposomes in Example 1 with ammonium sulfate, a monovalent counterion donor. A gradient across the lipid bilayer membrane of the liposome was established using 300 mM and 600 mM of ammonium sulfate, for remote loading of vinorelbine. The encapsulating (loading) efficiency and the retention profile of liposomal vinorelbine was assessed using in vitro plasma release method and the results are summarized in Table 1.

Results: The data shows ammonium sulfate was effective in loading or encapsulating vinorelbine in the liposome. However, ammonium sulfate was less effective in retaining vinorelbine in the liposome, with less than 30% of vinorelbine remain encapsulated in the liposome after 24 hours of plasma incubation.

TABLE 1

Characteristics of pharmaceutical compositions having monovalent counterion donors

| Pharmaceutical Composition | Monovalent Counterion Donor | Particle size [nm] | Encapsulation Efficiency [%] | % of encapsulated vinorelbine remaining after 24 h plasma incubation |
|---|---|---|---|---|
| LV001 | 300 mM ammonium sulfate | 93.3 | 93 | 28.7 |
| LV006 | 600 mM ammonium sulfate | 93.6 | 93 | 24.7 |

Example 3

Effect of Polyvalent Counterion Donor on the Encapsulation Efficiency and Retention Profile Sodium dextran sulfate with a molecular weight of 8,000 (8K) Daltons was converted to ammonium dextran sulfate (a pharmaceutically acceptable salt of dextran sulfate) by DOWEX ion exchange column. Two pharmaceutical compositions were prepared by mixing the liposomes in Example 1 with 4 mM and 8 mM of ammonium dextran sulfate respectively, followed by the remote loading of about 2 mg of Vinorelbine, incubated at about 60° C.

The encapsulating efficiency and the retention profile of liposomal vinorelbine in these two pharmaceutical compositions were assessed using in vitro plasma release method and the results are summarized in Table 2.

Results: 8 mM of ammonium dextran sulfate resulted in an encapsulation efficiency of 93%, whereas the encapsulating efficiency for 4 mM of ammonium dextran sulfate was below 90%. Similarly, LV009 formulation in Table 4 included polyvalent counterion donor only and had a less than 90% encapsulation efficiency and a retention rate of 98.74% 24 hours after plasma incubation.

TABLE 2

Characteristics of pharmaceutical compositions having polyvalent counterion donors.

| Pharmaceutical Composition | Polyvalent Counterion Donor Salt Ammonium dextran sulfate (MW = 8K) | Particle size (Nm) | Encapsulating Efficiency (%) |
|---|---|---|---|
| LV702 | 4 mM | 114 | 84 |
| LV703 | 8 mM | 114 | 93 |

Example 4

Effect of Combination of Mono- and Polyvalent Counterion Donors

An in vitro study was conducted to assess the combination of mono- and polyvalent counterion donors on the retention profile of liposomal vinorelbine.

Liposomes prepared according to Example 1 were mixed with 300 mM of ammonium sulfate (monovalent counterion donor) and various concentrations of sodium dextran sulfate (polyvalent counterion donor salt).

The encapsulating efficiency and the retention profile of various liposomal vinorelbines were assessed using 24-hour in vitro plasma release method and the results are summarized in Table 3.

Results: The data demonstrate that the various combinations of mono- and polyvalent counterion donors maintain the encapsulation efficiency of vinorelbine, and the liposome size was around 100 nm. In addition, the retention profile of liposomal vinorelbine depends on the concentration of the polyvalent counterion donor. 8 mM of sodium dextran sulfate is associated with a higher percentage of vinorelbine retention at 24 hours (78.9%) than that of 2 mM of sodium dextran sulfate (51.8%).

TABLE 3

Characteristics of liposomal vinorelbine with mono- and polyvalent counterion donor combination

| Pharmaceutical Composition | Types of counterion donor and concentration (mM) | | Particle size nm | Encapsulation Efficiency % | % of encapsulated vinorelbine remaining after 24 h plasma incubation % |
|---|---|---|---|---|---|
| | Ammonium Sulfate | Sodium Dextran Sulfate | | | |
| LV304 | 300 | 2 | 106.2 | 101.6 | 51.8 |
| LV302 | 300 | 4 | 104.5 | 106.3 | 67.3 |
| LV303 | 300 | 8 | 101.5 | 104.6 | 78.9 |

Example 5

Effect of Various Polyvalent Counterion Donor Salts

An in vitro study was conducted to assess the effect of different polyvalent counterion donor salts on the retention profile of liposome vinorelbine.

Liposomes prepared according to Example 1 were mixed with 300 mM of ammonium sulfate (AS) and two different polyvalent counterion donor salts: dextran sulfate (DS) sodium salt and DS ammonium salt.

The encapsulating efficiency and the retention profile of liposomal vinorelbine was assessed using 24-hour in vitro plasma release method and the results are summarized in Table 4.

Results: The data shows that sodium salt and ammonium salt of dextran sulfate were equally effective in retaining vinorelbine in the liposome after 24 hours of plasma incubation. In addition, when the concentration of polyvalent counterion donor or its salt is at 10 mM, the retention profile of the mono- and polyvalent counterion donor combination (100% and 94.2% of vinorelbine remaining in the liposome at 24 hours) was similar to that of polyvalent counterion donor composition (98.7% of vinorelbine remaining in the liposome after 24 hours). This is in contrast with the data in Table 3, wherein when the concentration of the polyvalent counterion donor was less than 10 mM, the retention profile of liposomal vinorelbine depends on the concentration of the polyvalent counterion donor.

Example 6

Effect of Various Molecular Weight of Polyvalent Counterion Donor

The effect of molecular weight of polyvalent counterion donor on liposomal vinorelbine retention profile was assessed. Liposomes prepared according to Example 1 were mixed with ammonium sulfate and 5K and 8K of dextran sulfate, respectively.

The encapsulating efficiency and the retention profile of liposomal vinorelbines were assessed using 24-hour in vitro plasma release method and the results are summarized in Table 5.

Results: The total valency of the polyvalent counterion donor affects the retention profile of liposomal vinorelbine. The data indicates that polyvalent counterion donor with higher valency is associated with more encapsulated vinorelbine at 24 hours.

TABLE 4

Characteristics of liposomal vinorelbine with mono- and polyvalent counterion donor combination

| Pharmaceutical Composition | Counterion Donor Combination | Particle size (nm) | Encapsulation Efficiency | % of encapsulated vinorelbine remaining after 24 h plasma incubation |
|---|---|---|---|---|
| LV007 | 300 mM AS/10 mM DS sodium salt | 112.7 | 85.1% | 100 |
| LV008 | 300 mM AS/10 mM DS ammonium salt | 114.1 | 83.7% | 94.2 |
| LV009 | 10 mM DS ammonium salt | 108.8 | 89.4% | 98.7 |

TABLE 5

Characteristics of liposomal vinorelbine with various molecular weight of polyvalent counterion donor.

| Pharmaceutical Composition | Ammonium Sulfate Concentration (mM) | Dextran Sulfate Concentration (mM)/molecular weight (K) | Particle size (nm) | Total Valency (mEq) | % of encapsulated vinorelbine remaining after 24 h plasma incubation |
|---|---|---|---|---|---|
| LV108 | 300 | 3 mM/5K | 110.0 | 73.68 | 55.9 |
| LV102 | 300 | 6 mM/5K | 114.5 | 147.36 | 67.7 |
| LV301 | 300 | 2 mM/8K | 106.2 | 78.64 | 51.8 |
| LV302 | 300 | 4 mM/8K | 104.5 | 157.28 | 67.3 |

Example 7

Adjustable Retention Profile Using Mono- and Polyvalent Counterion Donor Combination Various pharmaceutical compositions were prepared by mixing the liposomes in Example 1 with various concentrations of ammonium sulfate and various concentrations of dextran sulfate, followed by the remote loading of vinorelbine. The encapsulation efficiency and the retention profile of liposomal vinorelbine were assessed using 24-hour in vitro plasma release method and summarized in Tables 6-8.

Results of Table 6: At 72 hours, 72.2% of encapsulated vinorelbine still remained in NanoVNB composition (a pharmaceutical composition comprises polyvalent counterion donor octasulfate triethylamine only) and this high retention rate at 72 hours can lead to toxicity, most notably skin toxicity. On the other hand, all of the encapsulated vinorelbine was released in LV005 composition (a pharmaceutical composition comprises monovalent counterion donor only) at 72 hours, and this is associated with low therapeutic efficacy. By combining mono- and polyvalent counterion donors, a range of liposomal vinorelbine retention profile was obtained. It is noted the total equivalent of valency of the polyvalent counterion donor or its pharmaceutically acceptable salt is about 1 to about 240 mEq.

TABLE 6

Characteristics of pharmaceutical compositions with 100 mM and 300 mM of monovalent counterion donor and various concentrations of polyvalent counterion donor

| Pharmaceutical Composition | Dextran Sulfate MW | Dextran Sulfate mM | Total Valency mEq | Ammonium sulfate mM | % of encapsulated vinorelbine remaining At 24 h | % of encapsulated vinorelbine remaining At 72 h |
|---|---|---|---|---|---|---|
| LV005 | — | — | | 300 | 19.8 | N.D. |
| LV305 | 8K | 0.3 | 11.79 | 300 | 44.1 | 27.1 |
| LV306 | | 0.6 | 23.59 | | Not tested | 31.6 |
| LV301 | | 2 | 78.62 | | 59.2 | 44.4 |
| LV304 | | 3 | 117.93 | | 65.1 | Not tested |
| LV302 | | 4 | 157.24 | | 77.1 | 58.6 |
| LV303 | | 8 | 314.48 | | 90.1 | Not tested |
| LV402 | 1.6K | 0.25 | 1.97 | | 47.4 | 16.5 |
| LV403 | | 0.5 | 3.93 | | 53.5 | 20.7 |
| LV404 | | 1 | 7.86 | | 53.3 | 24.3 |
| LV401 | | 1.5 | 11.79 | | 39 | 20 |
| NanoVNB | 1.2K | 75 mM octasulfate triethylamine | 600 | — | 82.2 | 72.2 |
| LV307 | 8K | 6 | 235.86 | 300 | 49.1 | 19.6 |
| LV801 | 8K | 4 | 157.2 | 100 | 55.8 | 15.3 |

TABLE 7

Characteristics of the pharmaceutical compositions with various concentrations of monovalent counterion donor and a fixed concentration (0.3 mM) of polyvalent counterion donor

| Pharmaceutical Composition | Types of counterion donor and concentration (mM) | | Particle size nm | Encapsulation Efficiency % |
|---|---|---|---|---|
| | Ammonium Sulfate | Sodium Dextran Sulfate | | |
| LV801 | 50 | 0.3 | 102.3 | 44.4 |
| LV802 | 100 | 0.3 | 101.2 | 72.4 |
| LV803 | 200 | 0.3 | 106.9 | 102.8 |
| LV305 | 300 | 0.3 | 122.1 | 102.6 |
| LV804 | 400 | 0.3 | 106.1 | 87.9 |
| LV805 | 500 | 0.3 | 111.2 | 70.4 |
| LV806 | 600 | 0.3 | 106.5 | 48.3 |

Results of Table 7: the encapsulation efficiency of vinorelbine was above 70% using 100 mM to 500 mM of ammonium sulfate.

TABLE 8

Characteristics of the pharmaceutical compositions with various concentrations of monovalent counterion donor and a fixed concentration (0.3 mM) of polyvalent counterion donor

| Pharmaceutical Composition | Types of counterion donor and concentration (mM) | | Particle size nm | Encapsulation Efficiency % | % of encapsulated vinorelbine remaining after 24 h plasma incubation % |
|---|---|---|---|---|---|
| | Ammonium Sulfate | Sodium Dextran Sulfate | | | |
| NanoVNB | — | — | 97.2 | 100.9 | 80.3 |
| LV803 | 200 | 0.3 | 106.9 | 102.8 | 32.0 |
| LV305 | 300 | 0.3 | 122.1 | 102.6 | 44.1 |
| LV804 | 400 | 0.3 | 106.1 | 87.9 | 37.4 |

Results of Table 8: more than 30% of liposomal vinorelbine is retained after 24-hour of incubation using 200-400 mM of ammonium sulfate (monovalent counterion donor).

Example 8

In Vivo Anti-Cancer Evaluation Using HT-29 Human Colon Cancer Cells

An in vivo anti-cancer evaluation of the LV304 pharmaceutical composition was performed using an orthotopic HT-29 human colon tumor model in mice.

Mice had free access to drinking water and food at all time during this trial.

The study design involved 3 study groups as follows:

NanoVNB Group: 6 mice were given 25 mg/kg of vinorelbine as NanoVNB, once daily by intravenous injection on day 0, 3, 6 and 9.

LV304 Group: 6 mice were given 25 mg/kg of vinorelbine as LV304 pharmaceutical composition, once daily by intravenous injection on day 0, 3, 6 and 9.

Control Group: 6 mice were given a once daily intravenous saline injection on day 0, 3, 6 and 9.

During the study period, the following outcomes were measured:

Percentage of tumor growth change (% T/C). This was calculated by the following formula:

(Tumor weight$_{day\ x}$−Tumor weight$_{day\ 0}$)$_{treated}$/(Tumor weight$_{day\ x}$−Tumor weight$_{day\ 0}$)$_{control}$×100%.

Maximum body weight change, compare to the body weight on Day 0.

Mean tumor doubling time (TDT). This is widely used for quantification of tumor growth rate and is calculated by the following formula:

(day $x$−day 0)

day $x$ was the time taken for the tumor volume to double compared with the staging size.

Skin Toxicity Score, assessed and graded based on the parameters listed in Table 7.

TABLE 7

| | Skin Toxicity Score | |
|---|---|---|
| | Signs & Severity | |
| Grade | Hair loss & edema around the eyelid | Hair loss around the groin |
| 0 | None | None |
| 1 | Slight | Slight |
| 2 | Moderate | Moderate |
| 3 | Severe | Severe |
| 4 | Very severe | Very severe |

Result:

Table 8 shows the percentage of tumor growth change (% T/C) on day 8 was similar between NanoVNB and LV304 groups (−41.0% for NanoVNB and −42.4% LV304). The mean tumor doubling time (Mean TDT) was >78 days in the NanoVNB group, 67.1 days in LV304 group and 7.6 days in the control group. In addition, mice received LV304 displayed less side effects (less weight loss and lower skin toxicity score) relative to mice received NanoVNB.

Figure 2:
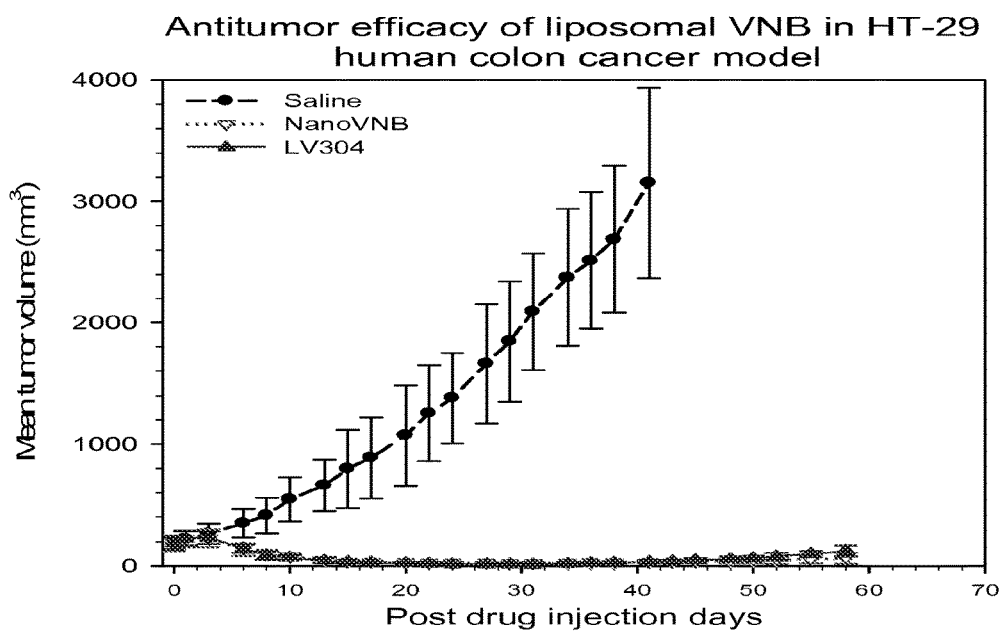
FIG. 2 shows the mean tumor volume in the NanoVNB group, the LV304 group and the saline (control) group.

FIG. 2 shows the mean tumor volume in the NanoVNB group, the LV304 group and the saline (control) group. The results indicate that the mean tumor volume in the NanoVNB and LV 304 groups were lower than 200 mm$^3$ throughout the study period, whereas the mean tumor volume in the control group exceeded 3000 mm$^3$ at day 40.

These results indicate that LV304 is an effective anti-cancer therapeutic agent relative to NanoVNB, but displayed less side effects.

TABLE 8

Anti-cancer evaluation of NanoVNB, LV304 and saline in HT-29 human colon cancer model

| Treatment Group | % T/C (day)* | Max. % BW change (day)* | Skin Toxicity Score (day)* | Mean TDT |
|---|---|---|---|---|
| Saline | — | −10.3 (34) | — | 7.0 ± 2.4 |
| NanoVNB | −41.0 ± 15.4 (8) | −20.8 (13) | 37 (17) | >78 |
| LV304 | −42.4 ± 13.1 (8) | −4.7 (13) | 20 (15) | 67.1 ± 5.4 |

*no. of days after Day 0

Example 9

In Vivo Anti-Cancer Evaluation Using PC14PE6/AS2 Human Lung Adenocarcinoma Orthotopic Model An in vivo anti-cancer evaluation of the LV304 pharmaceutical composition was performed using an orthotopic PC14PE6/AS2 lung tumor model in mice.

The study design involved 3 study groups as follows:

NanoNVB Group: 6 mice were given 50% of the maximum tolerated dose (MTD) of NanoVNB (½ MTD=7.5 mg/kg of vinorelbine) as a single intravenous injection on day 0.

LV304 Group: 6 mice were given 50% of the MTD of LV304 pharmaceutical composition (½ MTD=10 mg/kg of vinorelbine) as a single intravenous injection on day 0.

Control Group: 6 mice were given a single saline intravenous injection on day 0.

During the study period, the following outcomes were measured:

Maximum body weight change, compare to the body weight on Day 0.

Mean survival time.

Figure 3:
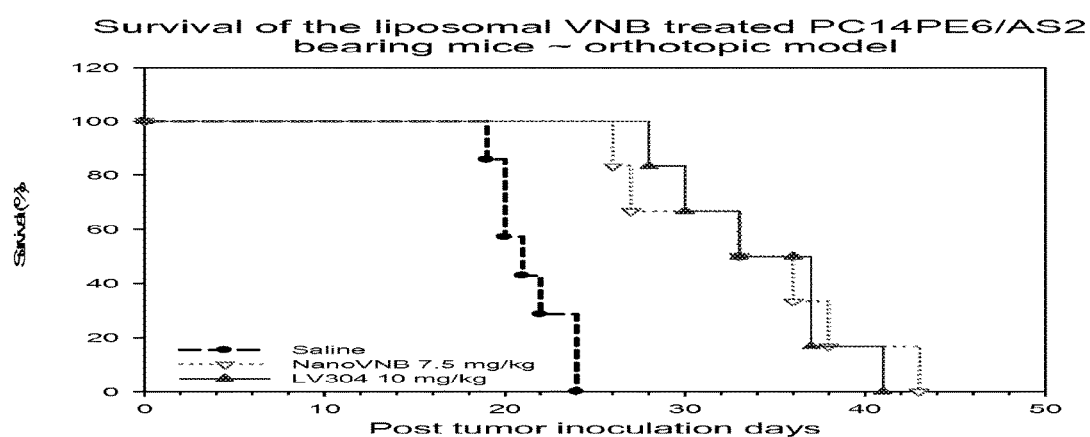
FIG. 3 shows the mean survival time in the NanoVNB group, the LV304 group and the saline (control) group.

Results: Referring to Table 9, the mean survival time for mice was 33.8 days after a single NanoVNB injection, 34.2 days after a single LV304 injection and 21.4 days after a single saline injection. FIG. 3 shows the survival time in NanoVNB group and LV304 group were significant longer from the saline (control) group (p<0.01).

TABLE 9

Anti-cancer evaluation of NanoVNB, LV304 and saline groups in PC14PE6/AS2 human lung adenocarcinoma orthotopic model.

| Treatment Group | Max. % BW change (day)* | Mean survival time ± SD (days) |
| --- | --- | --- |
| Saline | −3.6 (18) | 21.4 ± 2.0 |
| NanoVNB | −12.6 (9) | 33.8 ± 6.6 |
| LV304 | −17.0 (9) | 34.2 ± 4.8 |

*days after drug administration on day 0

Example 10

In Vivo Skin Toxicity Evaluation Using SCID Mouse Model

An in vivo skin toxicity evaluation of the LV304 pharmaceutical composition was performed using BALB/c mice. Mice had free access to drinking water and food at all time during this trial and were randomized into 3 study groups as follows:

NanoVNB Group: 6 mice received 7.5 mg/kg of vinorelbine as NanoVNB, through a daily IV injection on Day 0 and 9, 5 mg/kg on Day 3 and 6.

LV304 Group: 6 mice received 7.5 mg/kg of vinorelbine as LV304, through a daily IV injection on Day 0 and 9, 5 mg/kg on Day 3 and 6.

Control Group: 6 mice received once daily IV saline injection on Day 0, 3, 6 and 9.

During the study period, the skin toxicity was assessed and scored based on the grading system in Table 7.

Figure 4:
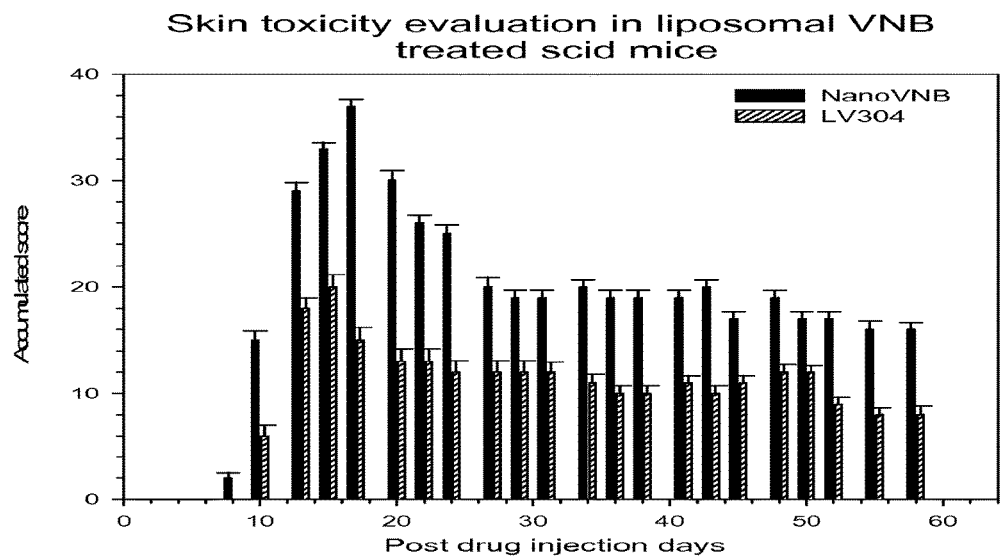
FIG. 4 shows the skin toxicity score in the NanoVNB group and the LV304 group.

Results: FIG. 4 shows the skin toxicity scores in the NanoVNB group and the LV304 group. The skin toxicity in the LV304 group was significantly less compare to the NanoVNB group during the 60 day trial period.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A pharmaceutical composition, comprising:
    at least one liposome having a particle forming component selected from a phospholipid or a mixture of at least one phospholipid and cholesterol;
    0.1 mM to 3.0 mM dextran sulfate or a pharmaceutically acceptable salt thereof;
    100 mM to 400 mM ammonium sulfate or a pharmaceutically acceptable salt thereof; and
    vinorelbine.

2. The pharmaceutical composition of claim 1, wherein the liposome further comprises a hydrophilic polymer with a long chain of highly hydrated flexible polymer attached to a phospholipid molecule.

3. The pharmaceutical composition of claim 1, wherein dextran sulfate has a molecular weight about 1,600 daltons to about 8,000 daltons.

\* \* \* \* \*